US010849499B2

(12) United States Patent
Ono

(10) Patent No.: US 10,849,499 B2
(45) Date of Patent: Dec. 1, 2020

(54) OPHTHALMOLOGIC APPARATUS AND METHOD OF CONTROLLING THE SAME

(71) Applicant: TOPCON CORPORATION, Tokyo (JP)

(72) Inventor: Yusuke Ono, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 228 days.

(21) Appl. No.: 16/115,577

(22) Filed: Aug. 29, 2018

(65) Prior Publication Data

US 2019/0059723 A1 Feb. 28, 2019

(30) Foreign Application Priority Data

Aug. 30, 2017 (JP) .................................. 2017-165518

(51) Int. Cl.
*A61B 3/15* (2006.01)
*A61B 3/00* (2006.01)
(Continued)

(52) U.S. Cl.
CPC ............ *A61B 3/152* (2013.01); *A61B 3/0025* (2013.01); *A61B 3/0075* (2013.01); *A61B 3/102* (2013.01); *A61B 3/113* (2013.01); *A61B 3/12* (2013.01)

(58) Field of Classification Search
CPC ....... A61B 3/152; A61B 3/0025; A61B 3/075; A61B 3/102; A61B 3/113; A61B 3/12
(Continued)

(56) References Cited

U.S. PATENT DOCUMENTS 7,555,151 B2 * 6/2009 Comaniciu ............ A61B 8/463
128/922
8,317,327 B2 * 11/2012 Cleveland .............. A61B 3/107
351/209
(Continued)

FOREIGN PATENT DOCUMENTS

EP 2702930 A1 * 3/2014 ............ G06T 7/337
EP 2702930 A1 3/2014
(Continued)

OTHER PUBLICATIONS

Extended European Search report dated Jan. 31, 2019, issued in corresponding EP Application No. 18190881.5, 8 pages.
(Continued)

*Primary Examiner* — James R Greece
(74) *Attorney, Agent, or Firm* — Xsensus LLP

(57) ABSTRACT

An ophthalmologic apparatus comprises an optical system that includes an optical scanner, deflects light from a light source using the optical scanner, projects the light onto a subject's eye, and receives light based on returning light from the subject's eye, a movement mechanism that moves the subject's eye and the optical system relative to each other, an image acquisition unit that acquires an image of the subject's eye, an abnormality detector that detects abnormality based on a reference image and the image of the subject's eye, a scan controller that controls the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected by the abnormality detector, and a tracking controller that controls the movement mechanism based on the reference image and the (Continued)

image of the subject's eye, when the abnormality is not detected by the abnormality detector.

13 Claims, 6 Drawing Sheets

(51) Int. Cl.
*A61B 3/12* (2006.01)
*A61B 3/10* (2006.01)
*A61B 3/113* (2006.01)

(58) Field of Classification Search
USPC .......................................................... 351/208
See application file for complete search history.

(56) References Cited

U.S. PATENT DOCUMENTS

| | | |
|---|---|---|
| 2009/0180073 A1 | 7/2009 | Ichikawa et al. |
| 2012/0033181 A1 | 2/2012 | Koizumi et al. |
| 2012/0229763 A1 | 9/2012 | Suehira et al. |
| 2014/0063460 A1 | 3/2014 | Borycki et al. |
| 2014/0211155 A1 | 7/2014 | Sakagawa et al. |
| 2015/0313468 A1 | 11/2015 | Okada et al. |
| 2015/0335234 A1 | 11/2015 | Okada et al. |
| 2016/0051139 A1 | 2/2016 | Sakagawa et al. |
| 2016/0198940 A1 | 7/2016 | Shibutani et al. |
| 2017/0100033 A1 | 4/2017 | Sakurada |
| 2017/0206657 A1* | 7/2017 | Nozato ................. G06K 9/4642 |

FOREIGN PATENT DOCUMENTS

| | | |
|---|---|---|
| EP | 2762060 A2 | 8/2014 |
| EP | 2 932 888 A1 | 10/2015 |
| EP | 2497409 A1 | 9/2019 |
| JP | 2009-131591 A | 6/2009 |
| JP | 2010-264225 A | 11/2010 |
| JP | 2015-043898 A | 3/2015 |
| JP | 2016-052386 A | 4/2016 |

OTHER PUBLICATIONS

Extended European Search Report dated Jul. 30, 2020, issued in corresponding European Patent Application No. 20168186.3.

* cited by examiner

OPHTHALMOLOGIC APPARATUS AND METHOD OF CONTROLLING THE SAME

CROSS-REFERENCE TO RELATED APPLICATION

This application is based upon and claims the benefit of priority from Japanese Patent Application No. 2017-165518, filed Aug. 30, 2017; the entire contents of which are incorporated herein by reference.

FIELD

Embodiments according to present invention described herein relate to an ophthalmologic apparatus and a method of controlling the same.

BACKGROUND

Examples of the ophthalmologic apparatus for photographing a subject's eye include an optical coherence tomography (OCT) apparatus using OCT, a fundus camera, a scanning laser ophthalmoscope (SLO), a slit lamp, and the like. Among them, OCT has been drawing attention. OCT creates an image representing the exterior structure, interior structure, or the like of a target eye using light beams from a laser light source or the like. Unlike X-ray computed tomography (CT), OCT is not invasive on the human body, and therefore is expected to be applied to the medical field and the biological field, in particular. For example, in the field of ophthalmology, apparatuses have been put to practical use for forming images of an anterior segment, etc. of the subject's eye or measuring the intraocular distance.

For the ophthalmologic apparatus like this, tracking is an important technique to obtain a high-definition image or to measure with high accuracy regardless of the eye movement of the subject's eye. Tracking is an operation to move the optical system of the apparatus according to eye movements of the subject's eye. To perform tracking, alignment and focusing are performed in advance. In other words, tracking is a function of maintaining a suitable positional relationship in which alignment and focusing are matched by causing the position of an optical system of the apparatus and the like to follow the eye movement.

In case that the movement or blinking of the subject's eye occurs during such tracking, it becomes difficult to continue the control of tracking. Thereby, accurate acquisition of images or accurate measurement can not be performed. For example, Japanese Unexamined Patent Application Publication No. 2010-264225, Japanese Unexamined Patent Application Publication No. 2009-131591, and Japanese Unexamined Patent Application Publication No. 2016-052386 disclose a method of reducing the influence on accurate acquisition of images or accurate measurement when movement or blinking of the subject's eye occurs.

Japanese Unexamined Patent Application Publication No. 2010-264225 discloses a fundus observation apparatus that obtains a displacement of a position of a fundus during scanning and corrects a position of an A-scan image acquired based on the obtained the displacement of the position.

Further, Japanese Unexamined Patent Application Publication No. 2009-131591 discloses a fundus camera that detects the occurrence of the blinking of the subject and sets a photographing timing after a predetermined time has elapsed from the detection timing of the occurrence of the blinking.

Further, Japanese Unexamined Patent Application Publication No. 2016-052386 discloses an ophthalmologic apparatus that predicts the occurrence cycle from the detection result of the occurrence of the blinking of the subject and allows data acquisition of the subject's eye based on the predicted cycle.

SUMMARY

The first aspect according to embodiments is an ophthalmologic apparatus comprising: an optical system that includes an optical scanner, deflects light from a light source using the optical scanner, projects the light onto a subject's eye, and receives light based on returning light from the subject's eye; a movement mechanism that moves the subject's eye and the optical system relative to each other; an image acquisition unit that acquires an image of the subject's eye; an abnormality detector that detects abnormality based on a reference image and the image of the subject's eye acquired by the image acquisition unit; a scan controller that controls the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected by the abnormality detector: and a tracking controller that controls the movement mechanism so that the optical system follows a movement of the subject's eye based on the reference image and the image of the subject's eye, when the abnormality is not detected by the abnormality detector.

Further, the second aspect according to the embodiments, in the first aspect, further may comprise an alignment controller that controls the movement mechanism to perform position matching of the optical system with respect to the subject's eye, when the abnormality is detected, wherein the scan controller may re-perform the first scan or the second scan, after the position matching by the alignment controller is completed.

Further, in the third aspect according to the embodiments, in the first aspect or the second aspect, the image acquisition unit may acquire an anterior segment image of the subject's eye, and the tracking controller may control the movement mechanism based on an amount of displacement of characteristic positions in the reference image and the anterior segment image.

Further, in the fourth aspect according to the embodiments, in the third aspect, the abnormality detector may detect the abnormality when the amount of displacement of the characteristic positions is equal to or larger than a first threshold value.

Further, in the fifth aspect according to the embodiments, in the third aspect or the fourth aspect, the abnormality detector may detect the abnormality when a characteristic point is not detected in the reference image or the anterior segment image.

Further, in the sixth aspect according to the embodiments, in any one of the third aspect to the fifth aspect, the abnormality detector may detect the abnormality when at least part of a boundary of a characteristic region is not detected in the reference image or the anterior segment image.

Further, in the seventh aspect according to the embodiments, in the first aspect or the second aspect, the image acquisition unit may acquire a fundus image of the subject's eye, and the tracking controller may control the movement mechanism so as to cancel an amount of displacement of positions obtained by performing a phase only correlation processing on the reference image and the fundus image.

Further, in the eighth aspect according to the embodiments, in the seventh aspect, the abnormality detector may detect the abnormality when a characteristic point is not detected based on luminance information of the reference image or the fundus image.

Further, in the ninth aspect according to the embodiments, in the seventh aspect or the eighth aspect, the abnormality detector may detect the abnormality when flare is detected in the reference image or the fundus image.

Further, the tenth aspect according to the embodiments, in any one of the first aspect to the ninth aspect, further may comprise a controller that stores abnormality occurrence information including a cause of the abnormality in a storage unit in association with subject information, when the abnormality is detected by the abnormality detector.

Further, the eleventh aspect according to the embodiments is a method of controlling an ophthalmologic apparatus comprising: an optical system that includes an optical scanner, deflects light from a light source using the optical scanner, projects the light onto a subject's eye, and receives light based on returning light from the subject's eye; a movement mechanism that moves the subject's eye and the optical system relative to each other. The method comprises: an image acquisition step of acquiring an image of the subject's eye; an abnormality detection step of detecting abnormality based on a reference image and the image of the subject's eye; a scan control step of controlling the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected: and a tracking control step of controlling the movement mechanism so that the optical system follows a movement of the subject's eye based on the reference image and the image of the subject's eye, when the abnormality is not detected.

The twelfth aspect according to the embodiments, in the eleventh aspect, further may comprise an alignment control step of controlling the movement mechanism to perform position matching of the optical system with respect to the subject's eye, when the abnormality is detected, wherein in the scan control step, the first scan or the second scan is re-performed, after the position matching in the alignment control step is completed.

The various features of the above aspects may be variously combined with some features included and others excluded to suit a variety of different applications.

DETAILED DESCRIPTION

Figure 1:
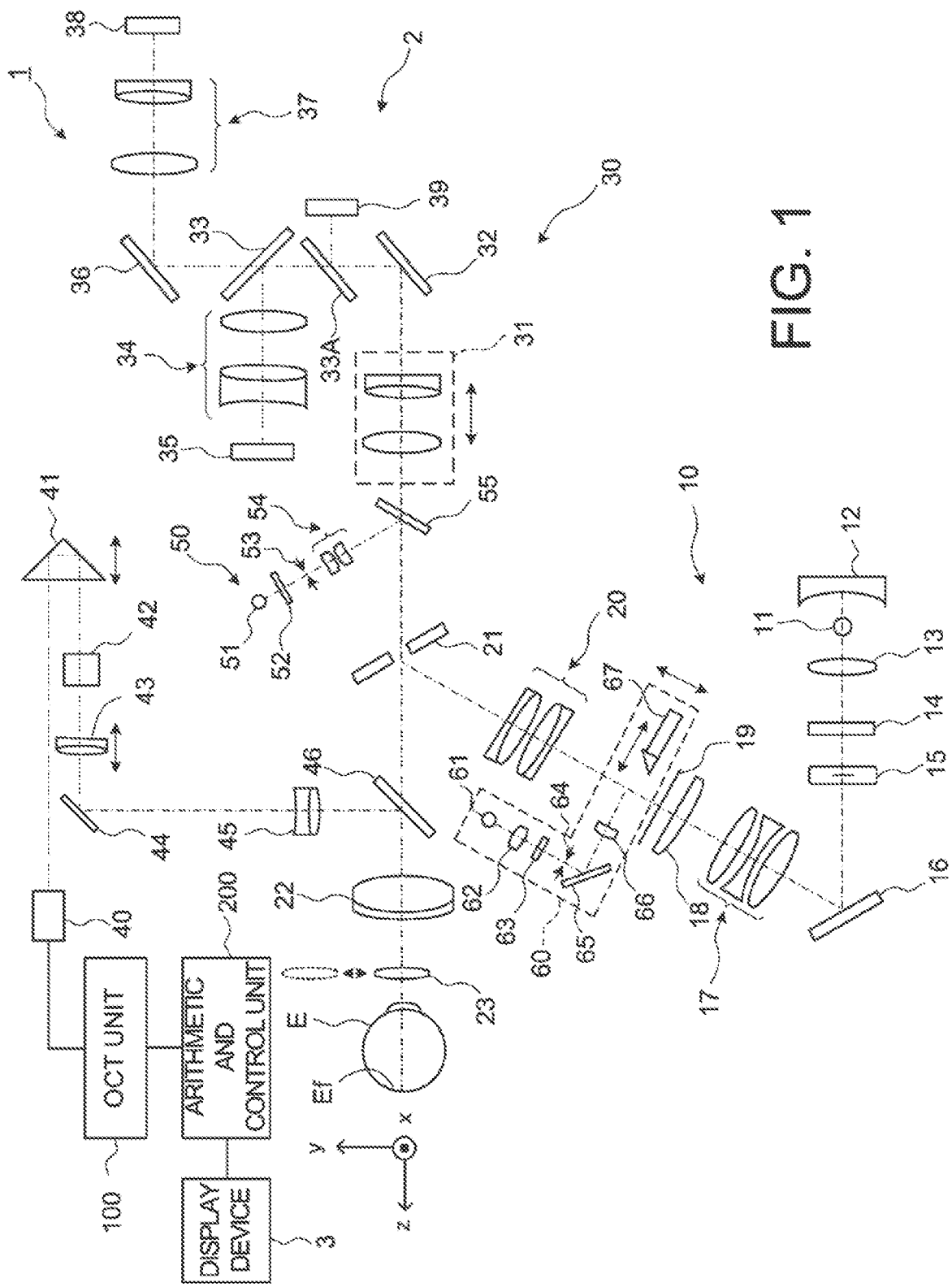
FIG. 1 is a schematic diagram illustrating an example of the configuration of an optical system of an ophthalmologic apparatus according to embodiments.

In the conventional method, the processing load for reducing the influence on the acquisition of images and the measurement is increased, or the control is complicated.

According to some embodiments of the present invention, influence on an accurate acquisition of an image and a measurement can be reduced with a simple control, even when movement or the like of a subject's eye occurs during the control of tracking.

Referring now to the drawings, exemplary embodiments of an ophthalmologic apparatus and a method of controlling the same according to the present invention are described below. Any of the contents of the documents cited in the present specification and arbitrary known techniques may be applied to the embodiments below.

An ophthalmologic apparatus according to the embodiments comprises an optical system that includes an optical scanner, deflects light from a light source by using the optical scanner, projects the deflected light onto the subject's eye, and receives light based on returning light from the subject's eye, the light including a part of the returning light, and can obtain information on the subject's eye. Such optical systems include OCT optical systems, SLO optical systems, and the like. The OCT optical system splits light from an OCT light source into measurement light and reference light, projects the measurement light onto a subject's eye via an optical scanner, and receives interference light between returning light of the measurement light from the subject's eye and the reference light having traveled through a reference optical path. The SLO optical system projects SLO light from an SLO light source onto a subject's eye via an optical scanner and receives returning light of the SLO light from the subject's eye.

Hereinafter, a case will be described where the ophthalmologic apparatus according to the embodiments is an ophthalmologic apparatus that images of a subject's eye by performing OCT on the subject's eye. However, embodiments are not limited thereto. For example, the ophthalmologic apparatus according to the embodiments may be capable of measuring the intraocular distance of a living eye such as the axial length by performing OCT on the subject's eye, or may be capable of forming an SLO image.

The ophthalmologic apparatus according to the embodiments is an ophthalmologic apparatus that is a combination of a Fourier domain OCT apparatus and a fundus camera. The ophthalmologic apparatus has a function of performing swept source OCT, but the embodiments are not limited to this. For example, the type of OCT is not limited to swept source OCT, and it may be the spectral domain OCT or the like. The swept source OCT is a technique that splits light from a wavelength tunable type (i.e., a wavelength scanning type) light source into measurement light and reference light; superposes the measurement light returning from the object to be measured with the reference light to generate interference light; detects the interference light with a balanced photodiode or the like; and applies the Fourier transform etc. to the detection data acquired through the tuning of wavelengths and the scanning of the measurement light to form an image. The spectral domain OCT is a technique that splits light from a low coherence light source into measurement light and reference light; superposes the measurement light returning from the object to be measured with the reference light to generate interference light; detects the spectral distribution of the interference light with a spectrometer; and applies the Fourier transform etc. to the detected spectral distribution to form an image.

The ophthalmologic apparatus according to the embodiments may include a scanning laser ophthalmoscope (SLO), a slit lamp microscope, an anterior segment photographing camera, a surgical microscope, a photocoagulator, etc. in place of or in addition to the fundus camera. In the present specification, a measuring by OCT is referred to as a "OCT measurement" and an image acquired using OCT is referred to as an OCT image. The optical path of the measurement light is denoted as a "measurement optical path", and the optical path of the reference light is denoted as a "reference optical path".

[Configuration]

As shown in FIG. 1, the ophthalmologic apparatus 1 according to the embodiments includes a fundus camera unit 2, an OCT unit 100, and an arithmetic and control unit 200. The fundus camera unit 2 has substantially the same optical system as the conventional fundus camera. The OCT unit 100 is provided with an optical system for performing OCT. The arithmetic and control unit 200 is provided with one or more processors for performing various kinds of arithmetic processing, control processing, and the like.

In the present specification, the term "processor" is used to mean, for example, a circuitry including a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), or the like. The processor realizes the function according to the embodiments, for example, by read out a computer program stored in a storage circuit or a storage device and executing the computer program.

[Fundus Camera Unit]

The fundus camera unit 2 is provided with an optical system for acquiring two dimensional images (fundus images) rendering the surface morphology of the fundus Ef of the subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. In addition, the fundus camera unit 2 is provided with an illumination optical system 10 and an imaging optical system 30. The illumination optical system 10 projects illumination light onto the fundus Ef. The imaging optical system 30 guides the illumination light reflected from the fundus Ef to imaging devices (CCD image sensors 35 and 38). Each of the CCD image sensors 35 and 38 is sometimes simply referred to as a "CCD". Further, the imaging optical system 30 guides measurement light coming from the OCT unit 100 to the subject's eye E, and guides the measurement light returning from the subject's eye E to the OCT unit 100.

The observation light source 11 of the illumination optical system 10 includes, for example, a halogen lamp or a light emitting diode (LED). The light (observation illumination light) output from the observation light source 11 is reflected by a reflective mirror 12 having a curved reflective surface, and becomes near-infrared light after passing through a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding area of an aperture part) of an aperture mirror 21, penetrates a dichroic mirror 46, and refracted by an objective lens 22, thereby illuminating the fundus Ef.

The observation illumination light reflected from the fundus Ef is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the fundus reflection light passes through a half mirror 33A, is reflected by a dichroic mirror 33, and forms an image on the light receiving surface of the CCD image sensor 35 by a condenser lens 34. The CCD image sensor 35 detects the fundus reflection light at a predetermined frame rate, for example. An image (observation image) based on the fundus reflection light detected by the CCD image sensor 35 is displayed on a display device 3. Note that when the imaging optical system 30 is focused on the anterior segment, reflection light of the observation illumination light from the anterior segment is detected by the CCD image sensor 35 and an observation image of the anterior segment based on the reflection light is displayed on the display device 3.

The imaging light source 15 is formed of, for example, a xenon lamp or an LED. The light (imaging illumination light) output from the imaging light source 15 is projected onto the fundus Ef via the same route as that of the observation illumination light. The imaging illumination light reflected from the fundus is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. The display device 3 displays an image (photographed image) based on the fundus reflection light detected by the CCD image sensor 38. Note that the same device or different devices may be used as the display device 3 for displaying an observation image and the display device 3 for displaying a photographed image. Besides, when similar photographing is performed by illuminating the subject's eye E with infrared light, an infrared photographed image is displayed. An LED may be used as the imaging light source. Note that when the imaging optical system 30 is focused on the anterior segment, reflection light of the observation illumination light from the anterior segment is detected by the CCD image sensor 38 and an observation image (photographed image) of the anterior segment based on the reflection light is displayed on the display device 3.

A liquid crystal display (LCD) 39 displays a fixation target and a visual target used for visual acuity measurement. The fixation target is a visual target for fixating the subject's eye E, and is used when performing fundus photography and OCT measurement, and the like.

Part of the light output from the LCD 39 is reflected by the half mirror 33A, is reflected by the mirror 32, travels through the photography focusing lens 31 and the dichroic mirror 55, and passes through the aperture part of the aperture mirror 21. The light having passed through the aperture part of the aperture mirror 21 penetrates the dichroic mirror 46, and is refracted by the objective lens 22, thereby being projected onto the fundus Ef. By changing the display position of the fixation target on the screen of the LCD 39, the fixation position of the subject's eye E can be changed.

Further, as with conventional fundus cameras, the fundus camera unit 2 is provided with an alignment optical system 50 and a focus optical system 60. The alignment optical system 50 generates an indicator (referred to as an alignment indicator) for the position adjustment (i.e., the alignment) of the optical system with respect to the subject's eye E. The focus optical system 60 generates an indicator (referred to as a split indicator) for adjusting the focus with respect to the subject's eye E.

The light output from an LED 51 of the alignment optical system 50 (i.e., alignment light) travels through the diaphragms 52 and 53 and the relay lens 54, is reflected by the dichroic mirror 55, and passes through the aperture part of the aperture mirror 21. The alignment light having passed through the aperture part of the aperture mirror 21 penetrates the dichroic mirror 46, and is projected onto the cornea of the subject's eye E by the objective lens 22.

The alignment light reflected from the cornea travels through the objective lens 22, the dichroic mirror 46 and the above-mentioned aperture part. Part of the cornea reflection light penetrates the dichroic mirror 55 and passes through the photography focusing lens 31. The cornea reflection light having passed through the photography focusing lens 31 is reflected by the mirror 32, penetrates the half mirror 33A, is reflected by the dichroic mirror 33, and is projected onto the light receiving surface of the CCD image sensor 35 by the condenser lens 34. The received image (i.e., alignment indicator image) captured by the CCD image sensor 35 is displayed on the display device 3 together with the observation image. A user conducts alignment by the same operation as performed on a conventional fundus camera. Instead, alignment may be performed in such a way that the arithmetic and control unit 200 analyzes the position of the alignment indicator and moves the optical system (automatic alignment).

The focus optical system 60 is movable along an optical path of the illumination optical system 10. The photography focusing lens 31 is movable along an optical path of the imaging optical system 30 in conjunction with the movement of the focus optical system 60. The reflection rod 67 of the focus optical system 60 can be inserted and removed into and from the illumination optical path.

To conduct focus adjustment, the reflective surface of the reflection rod 67 is arranged in a slanted position on the illumination optical path. The light output from the LED 61 of the focus optical system 60 (i.e., focus light) passes through the relay lens 62, is split into two light fluxes by the split indicator plate 63, passes through the two-hole diaphragm 64. The light having passed through the two-hole diaphragm 64 is reflected by the mirror 65, is converged on the reflective surface of the reflection rod 67 by the condenser lens 66, and is reflected by the reflective surface. The light reflected by the reflective surface of the reflection rod 67 travels through the relay lens 20, is reflected by the aperture mirror 21, penetrates the dichroic mirror 46, and is refracted by the objective lens 22, thereby being projected onto the fundus Ef as a pair of split indicator light(s).

The pair of split indicator light passing through a pupil of the subject's eye E reach the fundus Ef of the subject's eye E. The fundus reflection light of the pair of split indicator light passes through the pupil and passes through the same route as the fundus reflection light flux of the illumination light and is detected by the CCD image sensor 35. The received image (i.e., a pair of split indicator images) captured by the CCD image sensor 35 is displayed on the display device 3 together with the observation image. As in the conventional case, the arithmetic and control unit 200 can analyze positions of the pair of split indicator images, and move the focus optical system 60 for the focus adjustment (automatic focusing). A fundus image is formed on the imaging surface of the CCD image sensor 35 by moving the photography focusing lens 31 in conjunction with the movement of the focus optical system 60. Instead, the user may manually perform the focus adjustment while visually checking the pair of split indicator images (by operating the operation unit 240B described later).

The reflection rod 67 is inserted at a position on the illumination optical path substantially optically conjugate with the fundus Ef of the subject's eye E. The position of the reflective surface of the reflection rod 67 inserted in the optical path of the illumination optical system 10 is a position substantially optically conjugate with the split indicator plate 63. As described above, the split indicator light is split into two fluxes by the action of the two-hole diaphragm 64 and the like. When the fundus Ef and the reflective surface of the reflection rod 67 are not optically conjugate with each other, the pair of split indicator images acquired by the CCD image sensor 35 are displayed on the display device 3 in such a way that the split indicator images are separated in the right-and-left direction, for example. When the fundus Ef and the reflective surface of the reflection rod 67 are substantially optically conjugate with each other, the pair of split indicator images are displayed on the display device 3 in such a way that the positions of the split indicator images acquired by the CCD image sensor 35 coincide with each other in the vertical direction, for example. When the focus optical system 60 is moved along the illumination optical path so that the fundus Ef and the split indicator plate 63 are always optically conjugate with each other, the photography focusing lens 31 is moved along the imaging optical path in conjunction with the movement of the focus optical system 60. When the fundus Ef and the split indicator plate 63 are not optically conjugate with each other, the pair of split indicator images are separated into two. Thus, the position of the photography focusing lens 31 is obtained by moving the focus optical system 60 so that the pair of split indicator images coincide with each other in the vertical direction. In the present embodiment, the case where the pair of split indicator images are acquired has been described, but the number of split indicator images may be three or more.

The dichroic mirror 46 branches an optical path for OCT from an optical path for observing and imaging of the fundus. The dichroic mirror 46 reflects light of wavelengths used for OCT, and transmits light for observing and imaging of the fundus. The optical path for OCT is provided with, in order from the OCT unit 100 side, a collimator lens unit 40, an optical path length changing unit 41, an optical scanner 42, an OCT focusing lens 43, a mirror 44, and a relay lens 45.

The collimator lens unit 40 includes a collimator lens. The collimator lens unit 40 is optically connected to the OCT unit 100 with an optical fiber. The collimator lens in the collimator lens unit 40 is disposed at a position facing the emitting end of the optical fiber. The collimator lens unit 40 converts the measurement light LS (described later) emitted from the emitting end of the optical fiber into a parallel light flux and converges the returning light of the measurement light LS from the subject's eye E to the emitting end of the optical fiber.

The optical path length changing unit 41 is movable in directions indicated by the arrow in FIG. 1, thereby changing the length of the optical path for OCT measurement. This change in the optical path length is used for correcting the optical path length according to the axial length of the subject's eye E, adjusting the interference state, and the like. The optical path length changing unit 41 includes, for example, a corner cube and a mechanism for moving the corner cube.

The optical scanner 42 is disposed at a position optically conjugate with the pupil of the subject's eye E, for example. The optical scanner 42 changes the traveling direction of the light (measurement light LS) passing through the OCT optical path. Thereby, the subject's eye E can be scanned with the measurement light LS. The optical scanner 42 includes, for example, a galvano mirror that deflects the measurement light LS in the x direction, a galvano mirror that deflects the measurement light LS in the y direction, and a mechanism(s) that independently drives the galvano mirrors. Thereby, it is possible to scan with the measurement light LS in an arbitrary direction in the xy plane.

The OCT focusing lens 43 is movable along the optical path of the measurement light LS (an optical axis of an interference optical system).

The ophthalmologic apparatus 1 is provided with a front lens 23 capable of being arranged between the subject's eye E and the objective lens 22. The front lens 23 can be manually arranged between the subject's eye E and the objective lens 22. The front lens 23 may be capable to be arranged between the subject's eye E and the objective lens 22 under the control of a controller 210 described later. In the case that the front lens 23 is removed from between the subject's eye E and the objective lens 22, a focal position of the measurement light is located at the fundus Ef of the subject's eye E or in vicinity of the fundus Ef. Thereby, OCT measurement of the fundus Ef can be performed. In the case that the front lens 23 is arranged between the subject's eye E and the objective lens 22, a focal position of the measurement light is moved to the anterior segment or in vicinity of the anterior segment. Thereby. OCT measurement of the anterior segment can be performed.

[OCT Unit]

Figure 2:
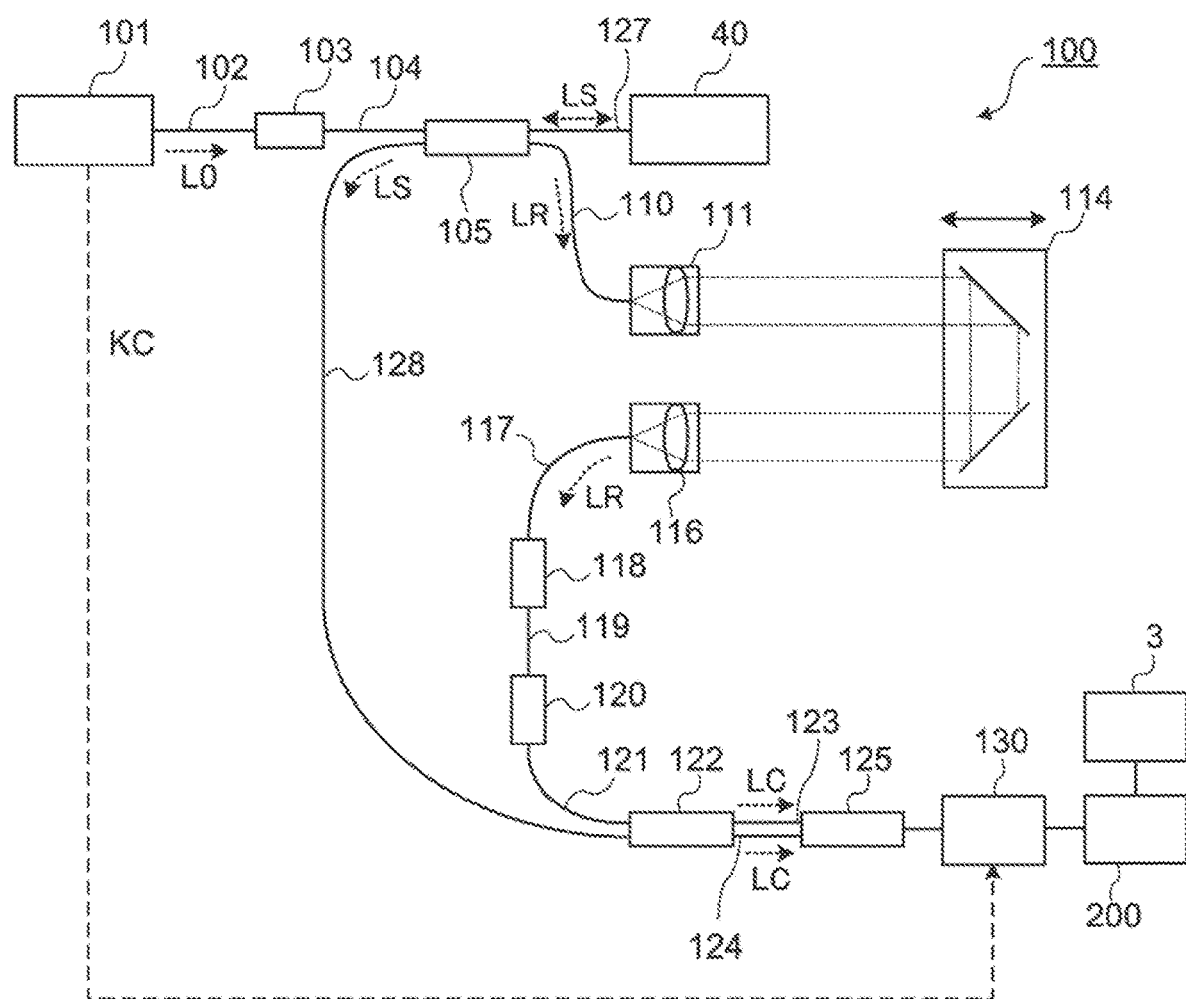
FIG. 2 is a schematic diagram illustrating an example of the configuration of an optical system of the ophthalmologic apparatus according to the embodiments.

Exemplary configuration of the OCT unit 100 is shown in FIG. 2. The OCT unit 100 includes an optical system for acquiring OCT images of the subject's eye E. This optical system is an interference optical system that splits light from the wavelength tunable type (wavelength scanning type) light source into the measurement light and a reference light, make the measurement light returning from the subject's eye E and the reference light having traveled through a reference optical path interfere with each other to generate interference light, and to detect the interference light. The detection result of the interference light obtained by the interference optical system (i.e., the detection signal) is an interference signal indicating the spectrum of the interference light, and is sent to the arithmetic and control unit 200.

Like swept source type ophthalmologic apparatuses commonly used, the light source unit 101 includes a wavelength tunable type (i.e., a wavelength scanning type) light source capable of sweeping (scanning) the wavelengths of emitted light. The wavelength tunable type light source includes a laser light source that includes a resonator. The light source unit 101 temporally changes the output wavelengths within the near infrared wavelength bands that cannot be visually recognized with human eyes.

Light L0 output from the light source unit 101 is guided to a polarization controller 103 through an optical fiber 102 and the polarization state thereof is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to a fiber coupler 105 through an optical fiber 104 and is split into the measurement light LS and the reference light LR.

The reference light LR is guided to a collimator 111 through an optical fiber 110 and becomes a parallel light flux. The reference light LR, which has become a parallel light flux, is guided to the optical path length changing unit 114. The optical path length changing unit 114 is movable in directions indicated by the arrow in FIG. 2, thereby changing the length of the optical path of the reference light LR. Through this movement, the length of the optical path of the reference light LR is changed. This change in the optical path length is used for correcting the optical path length according to the axial length of the subject's eye E, adjusting the interference state, and the like. The optical path length changing unit 114 includes, for example, a corner cube and a mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The configuration shown in FIG. 1 and FIG. 2 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

The reference light LR that has traveled through the optical path length changing unit 114 is converted from the parallel light flux to the convergent light flux by the collimator 116 and enters the optical fiber 117.

An optical path length correction member may be disposed in at least one of the reference optical path between the collimator 111 and the optical path length changing unit 114 and the reference optical path between the collimator 116 and the optical path length changing unit 114. The optical path length correction member functions as a delaying means for matching the optical path length (i.e., optical distance) of the reference light LR with the optical path length of the measurement light LS.

The reference light LR that has entered the optical fiber 117 is guided to the polarization controller 118. With the polarization controller 118, the polarization state of the reference light LR is adjusted. The polarization controller 118 has the same configuration as, for example, the polarization controller 103. The reference light LR whose polarization state has been adjusted by the polarization controller 118 is guided to an attenuator 120 through an optical fiber 119 and the light amount is adjusted under the control of the arithmetic and control unit 200. The reference light LR whose light amount is adjusted by the attenuator 120 is guided to a fiber coupler 122 through an optical fiber 121.

Meanwhile, the measurement light LS generated by the fiber coupler 105 is guided to the collimator lens unit 40 through an optical fiber 127, and is made into a parallel light flux by the collimator lens unit 40. The measurement light LS made into the parallel light flux is guided to the dichroic mirror 46 via the optical path length changing unit 41, the optical scanner 42, the OCT focusing lens 43, the mirror 44, and the relay lens 45. The measurement light LS guided to the dichroic mirror 46 is reflected by the dichroic mirror 46, is refracted by the objective lens 22, and is projected onto the subject's eye E. The measurement light LS is scattered (and reflected) at various depth positions of the subject's eye E. Returning light of the measurement light LS including such backscattered light advances through the same path as the outward path in the opposite direction and is guided to the fiber coupler 105, and then reaches the fiber coupler 122 through an optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light(s) LC by splitting the interference light generated from the measurement light LS and the reference light LR at a predetermined splitting ratio (for example, 1:1). The pair of interference light LC emitted from the fiber coupler 122 are guided to a detector 125 through optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. The clock KC is supplied from the light source unit 101 to the DAQ 130. The clock KC is generated in the light source unit 101 in synchronization with the output timing of each wavelength sweeping (i.e., wavelength scanning) within a predetermined wavelength range performed by the wavelength tunable type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic and control unit 200. For example, the arithmetic and control unit 200 performs the Fourier transform etc. on the spectral distribution based on the detection result obtained by the detector 125 for each series of wavelength scanning (i.e., for each A line). With this, the reflection intensity profile for each A line is formed. In addition, the arithmetic and control unit 200 forms image data by applying imaging processing to the reflection intensity profiles of the respective A lines.

[Arithmetic and Control Unit]

The configuration of the arithmetic and control unit 200 will be described. The arithmetic and control unit 200 analyzes the interference signals input from the detector 125 to form an OCT image of the subject's eye E. The arithmetic processing for the OCT image formation is performed in the same manner as in the conventional swept source type ophthalmologic apparatus.

Further, the arithmetic and control unit 200 controls the fundus camera unit 2, the display device 3, and the OCT unit 100. For example, the arithmetic and control unit 200 controls the display device 3 to display the OCT image of the subject's eye E.

Like conventional computers, the arithmetic and control unit 200 includes a microprocessor, a random access memory (RAM), a read only memory (ROM), a hard disk drive, a communication interface, and the like. The storage device such as a hard disk drive stores computer programs for controlling the ophthalmologic apparatus 1. The arithmetic and control unit 200 may include various kinds of circuitry such as a circuit board for forming OCT images, for example. In addition, the arithmetic and control unit 200 may include an operation device (input device) such as a keyboard and a mouse, and a display device such as an LCD.

[Processing System]

Figure 3:
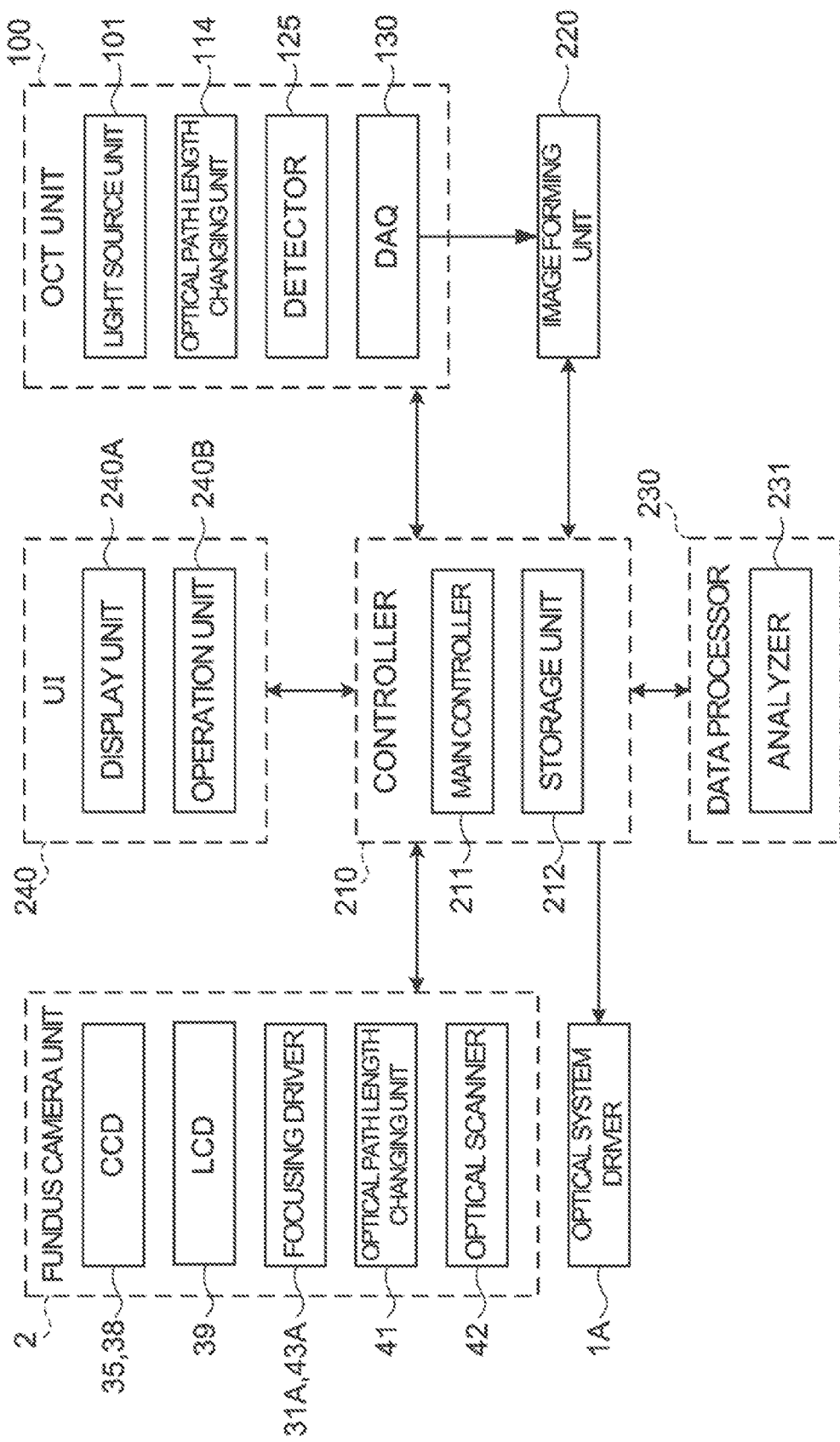
FIG. 3 is a schematic diagram illustrating an example of the configuration of a processing system of the ophthalmologic apparatus according to the embodiments.

The configuration of the processing system of the ophthalmologic apparatus 1 will be described with reference to FIGS. 3 and 4. In FIG. 3, some components of the ophthalmologic apparatus 1 are omitted, and the components particularly necessary for describing the present embodiment are selectively shown.

(Controller)

The arithmetic and control unit 200 includes the controller 210, an image forming unit 220, and a data processor 230. The controller 210 includes, for example, a microprocessor, a RAM, a ROM, a hard disk drive, a communication interface, and the like. The controller 210 is provided with a main controller 211 and a storage unit 212.

The functions of the main controller 211 is implemented by a microprocessor (i.e. a processor), for example. The storage unit 212 stores, in advance, a computer program for controlling the ophthalmologic apparatus. The computer program includes, for example, various light source control programs, optical scanner control program, various detector control programs, image forming program, data processing program, program for user interface, and the like. The main controller 211 operates according to the computer programs, and thereby the controller 210 performs the control processing.

(Main Controller)

The main controller 211 performs the various kinds of controls described above. In particular, as shown in FIG. 3, the main controller 211 controls components of the fundus camera unit 2 such as a focusing drivers 31A and 43A, the CCD image sensors 35 and 38, the LCD 39, the optical path length changing unit 41, and the optical scanner 42. In addition, the main controller 211 controls an optical system driver 1A. Further, the main controller 211 controls components of the OCT unit 100 such as the light source unit 101, the optical path length changing unit 114, the detector 125, and the DAQ 130.

The focusing driver 31A moves the photography focusing lens 31 along an optical axis of the imaging optical system 30 under the control of the main controller 211. The focusing driver 31A is provided with a holding member that holds the photography focusing lens 31, an actuator that generates a driving force for moving the holding member, and a transmission mechanism that transmits the driving force from the actuator to the holding member. The actuator may be a pulse motor, for example. The transmission mechanism may include a combination of gears, a rack and pinion, and the like, for example. As a result, the focusing driver 31A controlled by the main controller 211 moves the photography focusing lens 31, thereby the focus position of the imaging optical system 30 is changed. Note that the focusing driver 31A may be configured to move the photography focusing lens 31 along the optical axis of the imaging optical system 30 in accordance with a manual operation or the user's operation on the operation unit 240B.

The focusing driver 43A moves the OCT focusing lens 43 along the optical axis of the interference optical system (the optical path of the measurement light) in the OCT unit 100 under the control of the main controller 211. The focusing driver 43A is provided with a holding member that holds the OCT focusing lens 43, an actuator that generates a driving force for moving the holding member, and a transmission mechanism that transmits the driving force from the actuator to the holding member. The actuator may be a pulse motor, for example. The transmission mechanism may include a combination of gears, a rack and pinion, and the like, for example. As a result, the focusing driver 43A controlled by the main controller 211 moves the OCT focusing lens 43, thereby the focus position of the measurement light is changed. Note that the focusing driver 43A may be configured to move the OCT focusing lens 43 along the optical axis of the interference optical system in accordance with a manual operation or the user's operation on the operation unit 240B.

The main controller 211 can control an exposure time (charge accumulation time), a sensitivity, a frame rate, or the like of the CCD image sensor 35. The main controller 211 can control an exposure time, a sensitivity, a frame rate, or the like of the CCD image sensor 38.

The main controller 211 can control the LCD 39 to display fixation targets or visual targets for the visual acuity measurement. Thereby, the visual target presented to the subject's eye E can be switched, or type of the visual targets can be changed. Further, the presentation position of the visual target to the subject's eye E can be changed by changing the display position of the visual target on the screen of the LCD 39.

The main controller 211 can control the optical path length changing unit 41 to change relatively the difference between the length of the optical path of the reference light LR and the length of the optical path of the measurement light LS. The main controller 211 controls the optical path length changing unit 41 so as to render a target site of the subject's eye E in a predetermined range in the frame of an OCT image. Specifically, the main controller 211 can control the optical path length changing unit 41 so as to render the target site of the subject's eye E in a predetermined z position (a position in the depth direction) in the frame of the OCT image.

The main controller 211 can control the optical scanner 42 to change a projection position of the measurement light LS on the fundus Ef or the anterior segment of the subject's eye E.

The optical system driver 1A moves the optical system (the optical system shown in FIGS. 1 and 2) included in the ophthalmologic apparatus 1 three-dimensionally. The optical system driver 1A moves the optical system under the control of the main controller 211. This control is used in alignment and tracking. Here, tracking is to move the optical system of the apparatus according to the movement of the subject's eye E. To perform tracking, alignment and focusing are performed in advance. The tracking is performed by moving the optical system of the apparatus in real time according to the position and orientation of the subject's eye E based on the moving image obtained by imaging the subject's eye E, thereby maintaining a suitable positional relationship in which alignment and focusing are adjusted.

The main controller 211 can control the light source unit 101 to switch between lighting and non-lighting and to change light amount of the light L0, and the like.

The main controller 211 can control the optical path length changing unit 114 to change relatively the difference between the length of the optical path of the reference light LR and the length of the optical path of the measurement light LS. The main controller 211 controls the optical path length changing unit 114 so as to render a target site of the subject's eye E in a predetermined range in the frame of an OCT image. Specifically, the main controller 211 can control the optical path length changing unit 114 so as to render the target site of the subject's eye E in a predetermined z position in the frame of the OCT image. The main controller 211 can change relatively the difference between the length of the optical path of the reference light LR and the length of the optical path of the measurement light LS, by controlling at least one of the optical path length changing units 41 and 114. Hereinafter, a case will be described where the main controller 211 controls merely the optical path length changing unit 114 to adjust the difference of the optical path length between the measurement light LS and the reference light LR. However, the main controller 211 may control merely the optical path length changing unit 41 to adjust the difference of the optical path length between the measurement light LS and the reference light LR.

The main controller 211 can control an exposure time (charge accumulation time), a sensitivity, a frame rate, or the like of the detector 125. Further, the main controller 211 can control the DAQ 130.

Figure 4:
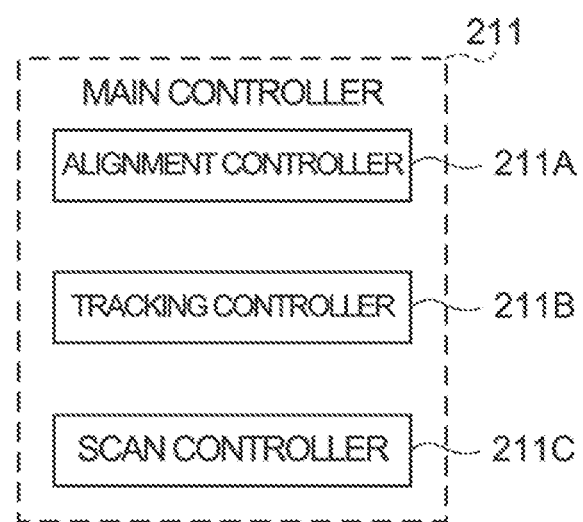
FIG. 4 is a schematic diagram illustrating an example of the configuration of a processing system of the ophthalmologic apparatus according to the embodiments.

As shown in FIG. 4, the main controller 211 includes an alignment controller 211A, a tracking controller 211B, and a scan controller 211C.

The alignment controller 211A controls perform of alignment for position matching of the optical system of the apparatus (the optical system shown in FIGS. 1 and 2) with respect to the subject's eye E. For example, the alignment indicator by the alignment optical system 50 and the split target by the focus optical system 60 are projected onto the subject's eye E respectively. A visual target image based on the alignment indicator is represented in the anterior segment image of the subject's eye E acquired by the imaging optical system 30. For example, the data processor 230 (described after) obtains a movement amount of the optical system of the apparatus based on a displacement of the position of the visual target image with respect to a reference position in the anterior segment image. The alignment controller 211A can control the optical system driver 1A based on the obtained movement amount.

Further, the alignment controller 211A can control the optical system driver 1A based on the anterior segment image acquired by the imaging optical system 30. For example, the alignment controller 211A specifies a characteristic position in the anterior segment image of the subject's eye E acquired by the imaging optical system 30 and obtains the movement amount of the optical system of the apparatus so as to cancel an amount of the displacement between the specified characteristic position and a predetermined target position. The alignment controller 211A controls the optical system driver 1A to perform position matching (registration) of the optical system of the apparatus with respect to the subject's eye E based on the obtained movement amount (xy directions). The target position may be a predetermined position, or a position designated by using the operation unit 240B in the anterior segment image.

In the same manner, the alignment controller 211A can control the optical system driver 1A to perform alignment based on the fundus image of the subject's eye E acquired by the imaging optical system 30.

For example, the alignment controller 211A can specify an in-focus state (a degree of blurring) of the anterior segment image (or the fundus image) of the subject's eye E acquired by the imaging optical system 30 and can obtain the movement amount of the optical system of the apparatus in the z direction so that the specified in-focus state becomes a desired in-focus state. The alignment controller 211A controls the optical system driver 1A to perform position matching of the optical system of the apparatus with respect to the subject's eye E based on the obtained movement amount (z direction). It should be noted that the anterior segment may be photographed from different directions each other by using two or more cameras, the in-focus state may be specified three-dimensionally from two or more images with parallax, and the movement amount in the z direction of the optical system of the apparatus may be obtained so that the specified in-focus state becomes a desired in-focus state.

The tracking controller 211B controls tracking with respect to the anterior segment image (or the fundus image) of the subject's eye E acquired by the imaging optical system 30. For example, the tracking controller 211B specifies a characteristic position in the anterior segment image (or the fundus image) at a predetermined timing and obtains a movement amount so as to cancel the amount of the displacement of the position when the specified characteristic position changes. The tracking controller 211B controls tracking with respect to the anterior segment image (or the fundus image) by controlling the optical system driver 1A based on the obtained movement amount.

In this embodiment, the tracking controller 211B performs control of tracking using a method corresponding to an observation site (imaging site, measurement site, acquiring site of data). When the front lens 23 is removed from between the subject's eye E and the objective lens 22, the tracking controller 211B performs control of tracking in a fundus mode. When the front lens 23 is arranged between the subject's eye E and the objective lens 22, the tracking controller 211B performs control of tracking in an anterior segment mode.

(Fundus Mode)

In the fundus mode, the tracking controller 211B performs control of tracking based on the fundus image of the subject's eye E acquired by the imaging optical system 30. The fundus images are acquired at different timings as a base image and a target image. The base image corresponds to the reference image. That is, the tracking controller 211B is capable of obtaining an amount of the displacement of the position (including a direction of the displacement of the position) of the target image, which is the anterior segment image obtained after acquiring the base image, with reference to the base image which is the anterior segment image of the subject's eye E obtained in advance, and of performing control of tracking based on the obtained amount of the displacement of the position. The tracking controller 211B can control the optical system driver 1A based on the obtained amount of the displacement of the position.

The amount of the displacement of the position of the target image with respect to the base image may be obtained by performing the phase only correlation processing on the base image and the target image. In this case, the amount of the displacement of the position includes a rotational movement amount at sub-pixel level (less than 1 pixel) in a rotation direction (rotation direction around the axis in the z direction) between the base image and the target image, a rotational movement direction thereof, a parallel movement amount at sub-pixel level in the xy plane between the base image and the target image, and a parallel movement direction thereof, and the like. In particular, the data processor 230 calculates a rotational movement amount and a rotational movement direction between the base image and the target image at the sub-pixel level by using the phase only correlation processing, and performs registration between the base image and the target image in the rotation direction based on the calculated rotational movement amount and the calculated rotational movement direction. The data processor 230 then calculates a parallel movement amount and a parallel movement direction between the base image and the target image, which have been registered to each other, at the sub-pixel level. Such the phase only correlation processing is similar to the processing disclosed in Japanese Unexamined Patent Application Publication No. 2015-043898.

(Anterior Segment Mode)

In the anterior segment mode, the tracking controller 211B performs control of tracking based on the anterior segment image of the subject's eye E acquired by the imaging optical system 30. The anterior segment images are acquired at different timings as a base image and a target image. The base image corresponds to the reference image. That is, the tracking controller 211B is capable of obtaining an amount of the displacement of the position (including a direction of the displacement of the position) of the target image, which is the anterior segment image obtained after acquiring the base image, with reference to the base image which is the anterior segment image of the subject's eye E obtained in advance, and of performing the control of tracking based on the obtained amount of the displacement of the position. The amount of the displacement of the position of the target image with respect to the base image may be obtained by performing the phase only correlation processing on the base image and the target image. The tracking controller 211B can control the optical system driver 1A based on the obtained amount of the displacement of the position.

The scan controller 211C controls the optical scanner 42 to change a projection position of the measurement light LS in a horizontal direction or a vertical direction (direction substantially perpendicular to the depth direction) of the observation site (the anterior segment or the fundus) of the subject's eye E. The scan controller 211C is capable of controlling a start position of each scan, an end position of each scan, and a deflection angle of the measurement light LS with respect to the optical scanner 42 based on a preset scan area and a scan pattern.

In the embodiments, examples of scan modes by the measurement light LS include horizontal scan, vertical scan, cross scan, radial scan, circle scan, concentric scan, helical (spiral) scan, and the like. These scan modes are selectively used in consideration of a site of the anterior segment or the fundus to be observed, an object to be analyzed (thickness of retina, etc.), time required for scan, accuracy of scan, or the like.

In the horizontal scan mode, the projection position of the measurement light LS is changed in the horizontal direction (x direction). The horizontal scan mode includes scans which changes the projection position of the measurement light LS along a plurality of horizontal scan lines arranged in the vertical direction (y direction). In this mode, the intervals between the horizontal scan lines may be set as desired. The intervals of the horizontal scan lines may be set sufficiently small to form a three-dimensional image. Such a scan mode is referred to as three-dimensional scan. These items for the horizontal scan mode may be applied to the vertical scan mode in similar ways.

In the cross scan mode, the projection position of the measurement light LS is changed along a cruciform trajectory consisting of two straight trajectories (line trajectories) which are perpendicular to each other. In the radial scan mode, the projection position of the measurement light LS is changed along radial trajectories consisting of a plurality of line trajectories arranged at a predetermined angle. The cross scan mode is an example of the radial scan mode.

In the circle scan mode, the projection position of the measurement light LS is changed along a circular trajectory. In the concentric scan mode, the projection position of the measurement light LS is changed along a plurality of circular trajectories arranged concentrically around a predetermined center position. The circle scan can be considered as a special example of the concentric scan. In the helical scan mode, the projection position of the measurement light LS is changed along a helical (spiral) trajectory while the rotation radius is gradually reduced (or increased).

In the embodiments, as described after, a state in which it is difficult to continue controlling tracking such as movement of the subject's eye, occurrence of blinking, or the like is detected as an abnormal state based on the anterior segment image or the fundus image. At least one of the tracking controller 211B and the scan controller 211C can perform the following control based on the detection result of the above abnormal state.

When the above abnormality is no detected, the tracking controller 211B controls the optical system driver 1A so as to cause the optical system of the apparatus to follow the movement of the subject's eye based on the base image and the target image. On the other hand, when the above abnormality is detected, the scan controller 211C controls the optical scanner 42 to re-perform a first scan, which is being performed at an acquisition timing of the target image, or a second scan, which is performed before the first scan, so as to project the measurement light LS onto a start position of the first scan or a start position of the second scan. Here, the first scan may be a horizontal scan, a vertical scan, a cross scan, a radial scan, a circle scan, a concentric scan, or a helical (spiral) scan. The second scan may be a scan performed immediately before the first scan or a scan performed two or more scans before the first scan. The second scan may be a scan performed in the past by a predetermined time from the first scan, in consideration of processing load and control complexity. The second scan may also be a horizontal scan, a vertical scan, a cross scan, a radial scan, a circle scan, a concentric scan, or a helical (spiral) scan, as well the first scan. Here, the scan controller 211C may re-perform the first scan or the second scan, after position matching of the optical system of the apparatus with respect to the subject's eye is completed by the alignment controller 211A. The scan controller 211C can perform rescan in scan units in a direction crossing the measurement light LS.

(Storage Unit)

The storage unit 212 stores various types of data. Examples of the data stored in the storage unit 212 include, for example, image data of an OCT image, image data of a fundus image and an anterior segment image, and subject's eye information (subject information). The subject's eye information includes information on the subject such as patient ID and name, and information on the subject's eye such as identification information of the left eye/right eye. The main controller 211 can store abnormality occurrence information (described after) in the storage unit 212 in association with the subject's eye information. The storage unit 212 further stores data such as various types of programs and control information to run the ophthalmologic apparatus 1.

(Image Forming Unit)

The image forming unit 220 forms image data of tomographic images of the fundus Ef and the anterior segment based on interference signals from the detector 125 (DAQ 130). The image formation processing includes noise removal (noise reduction), filtering, fast Fourier transform (FFT), and the like. The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

Further, the image forming unit 220 can form an anterior segment image based on the detection result of the reflection light from the anterior segment of the subject's eye E obtained by the CCD image sensor 35 or the CCD image sensor 38.

The image forming unit 220 includes, for example, the circuitry described above. Incidentally, "image data" and an "image" based thereon may be treated in the same way in this specification. Further, a site of the subject's eye E and an image thereof may also be treated in the same way.

(Data Processor)

The data processor 230 performs various kinds of data processing (e.g., image processing) and various kinds of analysis processing on an image formed by the image forming unit 220. For example, the data processor 230 performs various correction processes such as brightness correction and dispersion correction of images.

The data processor 230 can form volume data (voxel data) of the subject's eye E by performing known image processing such as interpolation processing for interpolating pixels between tomographic images. In the case of displaying an image based on the volume data, the data processor 230 performs a rendering processing on the volume data so as to form a pseudo three-dimensional image viewed from a specific line-of-sight direction.

The data processor 230 can perform registration (i.e., position matching) between a fundus image (or an anterior segment image) and an OCT image. When the fundus image (or the anterior segment image) and the OCT image are obtained in parallel, the registration between the fundus image (or the anterior segment image) and the OCT image, which have been (almost) simultaneously obtained, can be performed using the optical axis of the imaging optical system 30 as a reference. Such registration can be achieved since the optical system for the fundus image (or the anterior segment image) and that for the OCT image are coaxial. Besides, regardless of the timing of obtaining the fundus image (or the anterior segment image) and that of the OCT image, the registration between the OCT image and the fundus image (or the anterior segment image) can be achieved by performing the registration between the fundus image (or the anterior segment image) and a front image formed by projecting at least part of an image area corresponding to the fundus Ef (or the anterior segment image) in the OCT image onto the xy plane. This registration method can also be employed when the optical system for acquiring fundus image (or the anterior segment image) and the optical system for OCT are not coaxial. Further, when both the optical systems are not coaxial, if the relative positional relationship between these optical systems is known, the registration can be performed with referring to the relative positional relationship in a manner similar to the case of coaxial optical systems.

The data processor 230 includes an analyzer 231. The analyzer 231 executes a predetermined analysis processing based on the anterior segment image or the fundus image obtained by the imaging optical system 30. The analysis processing includes processing for specifying a characteristic region or a characteristic position (characteristic point) in the image, processing for detecting movement of the subject's eye, detecting occurrence of blinking, or detecting occurrence of flare, or the like.

(Anterior Segment Mode)

In the anterior segment mode, the analyzer 231 performs a processing for specifying the characteristic region or the characteristic position in the anterior segment image, for example.

For example, the analyzer 231 can specify a predetermined region including a region corresponding to the pupil of the subject's eye E in the anterior segment image as the characteristic region. The tracking controller 211B controls the optical system driver 1A based on the displacement of the characteristic region in the target image with respect to the characteristic region in the base image. Thereby, performing tracking based on the position of the characteristic region can be achieved. Examples of the characteristic region include a blood vessel, a diseased site, an iris region, and the like.

Further, the analyzer 231 is capable of detecting occurrence of cause which inhibits (hinders) the control of tracking such as the movement of the subject's eye E, occurrence of blinking, or the like, by analyzing the base image and the target image. For example, when the movement amount of the characteristic region in the target image with respect to the characteristic region in the base image is equal to or larger than a first threshold value, the analyzer 231 determines that the movement amount of the subject's eye E is large and detects as the abnormal state in which the control of tracking is inhibited. Further, when a predetermined characteristic region can not be specified (detected) in at least one of the base image and the target image, the analyzer 231 determines that an eyelid is closed by blinking and detects as the abnormal state in which the control of tracking is inhibited. Further, when at least part of a boundary of a characteristic region (for example, pupil region) can not be specified (detected) in at least one of the base image and the target image, the analyzer 231 determines that an eyelash is represented in the image and detects as the abnormal state in which the control of tracking is inhibited.

(Fundus Mode)

In the fundus mode, the analyzer 231 performs a processing for specifying the characteristic region or the characteristic position in the fundus image, for example.

For example, the analyzer 231 can specify a predetermined region including a region corresponding to the optic disc or the central fovea of the subject's eye E in the fundus image as the characteristic region. The tracking controller 211B controls the optical system driver 1A based on the displacement of the characteristic region in the target image with respect to the characteristic region in the base image. Thereby, performing tracking based on the position of the characteristic region can be achieved. Examples of the characteristic region include a blood vessel, a diseased site, and the like.

Further, as in the case of the anterior segment mode, the analyzer 231 is capable of detecting occurrence of cause which inhibits the control of tracking such as the movement of the subject's eye E, occurrence of blinking, occurrence of flare, or the like, by analyzing the base image and the target image. For example, when the movement amount of the characteristic region in the target image with respect to the characteristic region in the base image is equal to or larger than a second threshold value, the analyzer 231 determines that the movement amount of the subject's eye E is large and detects as the abnormal state in which the control of tracking is inhibited. Further, the analyzer 231 is capable of specifying (detecting) a predetermined characteristic region by analyzing luminance distribution (luminance information) of at least one of the base image and the target image. For example, when the brightness of the whole image is high (equal to or larger than a predetermined threshold value level), the analyzer 231 determines that an eyelid is closed by blinking and detects as the abnormal state in which the control of tracking is inhibited. For example, when the brightness of the whole image is low (equal to or less than a predetermined threshold value level), the analyzer 231 determines that an eyelash is represented in the image and detects as the abnormal state in which the control of tracking is inhibited. For example, when a partial region with high brightness is present, the analyzer 231 determines that flare occurs in the image and detects as the abnormal state in which the control of tracking is inhibited.

The data processor 230 that functions as above includes, for example, a microprocessor, a RAM, a ROM, a hard disk drive, a circuit board, and the like. In a storage device such as the hard disk drive, a computer program for causing the microprocessor to execute the functions described above is stored in advance.

(User Interface)

A user interface 240 includes the display unit 240A and the operation unit 240B. The display unit 240A includes the aforementioned display device of the arithmetic and control unit 200 and the display device 3. The operation unit 240B includes the aforementioned operation device of the arithmetic and control unit 200. The operation unit 240B may include various types of buttons and keys provided on the case of the ophthalmologic apparatus 1 or the outside. Besides, the display unit 240A may include various types of displays such as a touch panel and the like arranged on the case of the fundus camera unit 2.

Note that the display unit 240A and the operation unit 240B need not necessarily be formed as separate devices. For example, a device like a touch panel, which has a display function integrated with an operation function, can be used. In such cases, the operation part 240B includes the touch panel and a computer program. The content of operation performed on the operation unit 240B is fed to the controller 210 in the morphology of an electrical signal. Moreover, operations and inputs of information may be performed by using a graphical user interface (GUI) displayed on the display unit 240A and the operation unit 240B.

The optical system 100 (for example, the interference optical system included in the OCT unit 100) as shown in FIG. 1 is an example of the "optical system" according to the embodiments. The optical system driver 1A is an example of the "movement mechanism" according to the embodiments. The imaging optical system 30 is an example of the "image acquisition unit" according to the embodiments. The analyzer 231 is an example of the "abnormality detector" according to the embodiments. The base image is an example of the "reference image" according to the embodiments. The target image is an example of the "image of the subject's eye acquired by the image acquisition unit".

Operation Example

Described below is an example of the operation of the ophthalmologic apparatus according to the embodiments.

Figure 5:
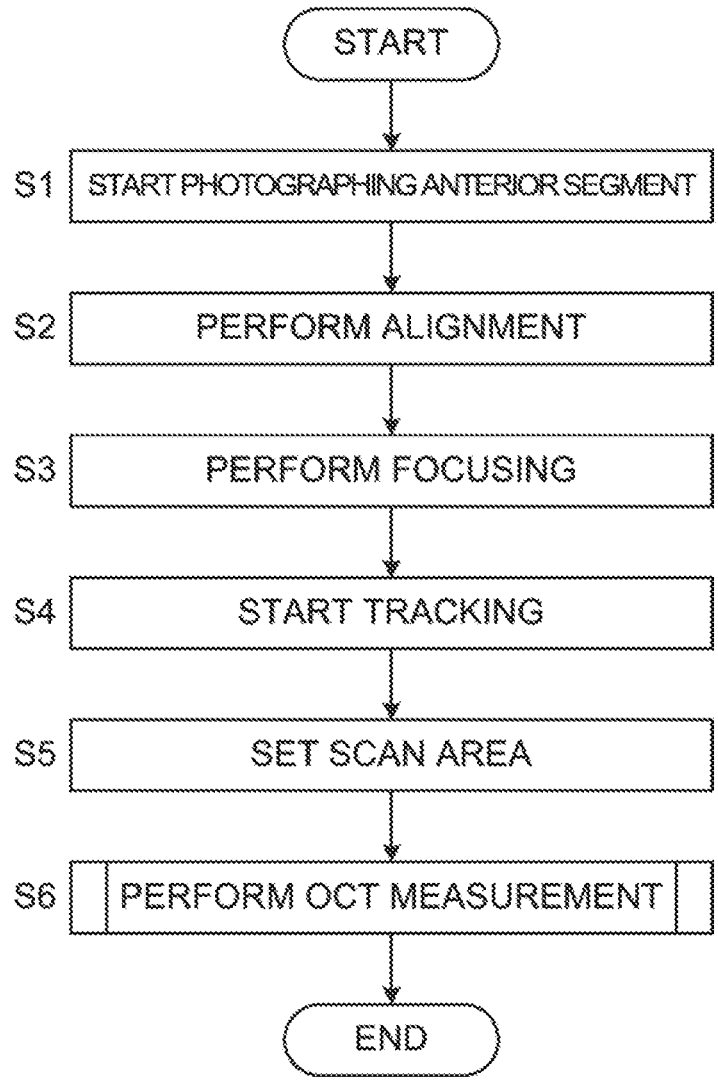
FIG. 5 is a flow chart of an operation example of the ophthalmologic apparatus according to the embodiments.

FIG. 5 shows a flow chart of an operation example of the ophthalmologic apparatus 1 according to the embodiments. In FIG. 5, the front lens 23 is arranged between the subject's eye E and the objective lens 22.

(S1: Start Photographing Anterior Segment)

First, the anterior segment is continuously irradiated with the illumination light from the observation light source 11 (near-infrared light through the action of the visible cut filter 14), thereby starting the acquisition of a near-infrared moving image of the anterior segment. The near-infrared moving image is acquired in real time until the end of the continuous illumination. The frames of the moving image are temporarily stored in a frame memory (the storage unit 212) and sequentially sent to the data processor 230.

Incidentally, the alignment indicator and the split target are projected onto the eye E respectively by the alignment optical system 50 and the focus optical system 60. Accordingly, the alignment indicator and the split target are illustrated in the near-infrared moving image. Alignment and focusing can be performed using them. The fixation target is also projected onto the subject's eye E by the LCD 39. The subject is instructed to fixate the eye on the fixation target.

(S2: Perform Alignment)

The data processor 230 sequentially analyzes the frames successively acquired by shooting a moving image of the subject's eye E with the optical system to find the position of the visual target image based on the alignment indicator, thereby calculating the movement amount of the optical system. The controller 210 controls the optical system driver 1A based on the movement amount of the optical system obtained by the data processor 230 to perform automatic alignment.

(S3: Perform Focusing)

The data processor 230 sequentially analyzes the frames successively acquired by shooting a moving image of the subject's eye E with the optical system to find the position of the split target, thereby calculating the movement amounts of the photography focusing lens 31 and the OCT focusing lens 43. The controller 210 controls the focusing drivers 31A and 43A based on the movement amounts of the photography focusing lens 31 and the OCT focusing lens 43 obtained by the data processor 230 to perform automatic focusing.

(S4: Start Tracking)

Subsequently, the controller 210 starts the control for automatic tracking. Specifically, the data processor 230 analyzes the frames successively acquired by shooting a moving image of the subject's eye E with the optical system in real time, and monitors the movement (positional change) of the subject's eye E. The controller 210 controls the optical system driver 1A to move the optical system in accordance with the position of the subject's eye E sequentially obtained. Thereby, the optical system can follow the movement of the subject's eye E in real time. Thus, it is possible to maintain a good positional relationship with proper alignment and focus.

(S5: Set Scan Area)

The controller 210 displays the near-infrared moving image on the display unit 240A in real time. The user sets a scan area on the near-infrared moving image using the operation part 240B. The scan area may be one- or two-dimensional.

(S6: Perform OCT Measurement)

The controller 210 controls a light source unit 101 and the optical path length changing unit 41 as well as controlling the optical scanner 42 based on the scan area set in step S5 to perform OCT measurement of the anterior segment. The image forming unit 220 forms a tomographic image of the anterior segment based on a detection signal obtained. If three-dimensional scan is set as the scan mode, the data processor 230 forms a three-dimensional image of the anterior segment based on a plurality of tomographic images formed by the image forming unit 220. It should be noted that, when the abnormal state in which the control of tracking is inhibited, the controller 210 perform rescan. Thereby, the influence on acquisition of the image and measurement can be reduced. Then, the operation example is completed (END).

Figure 6:
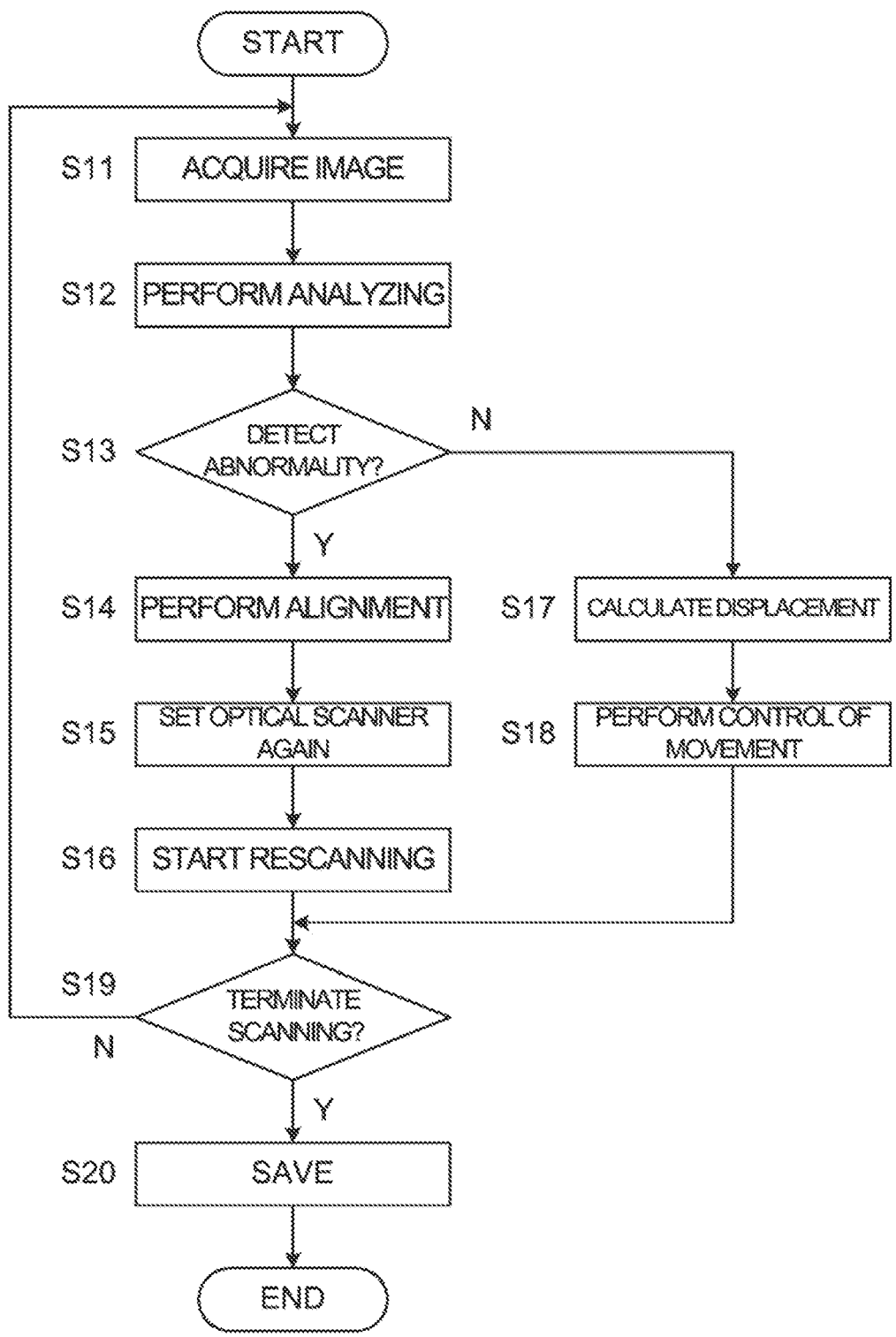
FIG. 6 is a flow chart of an operation example of the ophthalmologic apparatus according to the embodiments.

FIG. 6 illustrates an example of the flow of step S6 in FIG. 5. In FIG. 6, it is assumed that the anterior segment image as the base image has been acquired in advance.

(S11: Acquire Image)

First, the controller 210 controls the imaging optical system 30 to acquire the anterior segment image as the target image.

(S12: Perform Analyzing)

Subsequently, the controller 210 controls the analyzer 231 to analyze the anterior segment image as the base image that has been acquired already and the anterior segment image acquired in step S11 and to detect whether or not it is the abnormal state in which the control of tracking is inhibited.

(S13: Detect Abnormality?)

When it is determined that the abnormal state is present by the analyzing processing in step S12 (S13: Y), the operation of the ophthalmologic apparatus 1 moves to step S14. When it is determined that the abnormal state is not present by the analyzing processing in step S12 (S13: N), the operation of the ophthalmologic apparatus 1 moves to step S17.

(S14: Perform Alignment)

When it is determined that the abnormal state is present (S13: Y), the controller 210 performs alignment in the same manner as in step S2. Thereby, the positional relationship of the optical system of the apparatus with respect to the subject's eye E becomes substantially the same as that after the completion of alignment in step S2.

(S15: Set Optical Scanner Again)

Subsequently, the controller 210 sets the optical scanner 42 again so as to project the measurement light LS onto the start position of the first scan, which is being performed at the acquisition timing of the image in step S11, or the start position of the second scan performed before the first scan.

(S16: Start Rescanning)

Next, the controller 210 re-performs the first scan or the second scan from the start position set again in step S15.

(S17: Calculate Displacement)

When it is determined that the abnormal state is not present (S13: N), the controller 210 controls the analyzer 231 to calculate the displacement between the characteristic region in the anterior segment image as the base image that has been acquired already and the characteristic region in the anterior segment image acquired in step S11.

(S18: Perform Control of Movement)

The controller 210 controls the optical system driver 1A to cause the optical system of the apparatus to follow the movement of the subject's eye based on the calculated displacement in step S17.

(S19: Terminate Scanning?)

After step S16 or step S18, the controller 210 determines whether or not the scanning is to be terminated. For example, the controller 210 determines whether or not the scanning is to be terminated based on a preset scan area and scan pattern. Having determined that the scanning is to be terminated (S19: Y), the operation of the ophthalmologic apparatus 1 moves to step S20. Having determined that the scanning is not to be terminated (S19: N), the operation of the ophthalmologic apparatus 1 moves to step S11.

(S20: Save)

Having determined that the scanning is to be terminated (S19: Y), the controller 210 stores abnormality occurrence information including a cause of occurrence of the abnormal state in the storage unit 212 in association with subject information, based on the detection processing of the abnormal state in step S13. As described above, the analyzer 231 detects the occurrence of the movement of the subject's eye E or the occurrence of blinking, as the abnormal state. The analyzer 231 can generate the abnormality occurrence information including occurrence cause information corresponding to the processing in which the abnormal state is detected. When abnormal states of the same type are continuously detected a predetermined times at the time of measurement of the subject, the analyzer 231 can generate the abnormality occurrence information including the occurrence cause information corresponding to the abnormal state. It should be noted that step S20 may be performed at an arbitrary timing between step S13 and step S19. With this, the processing of step S6 is terminated (END).

In FIG. 6, the case where the observation site is the anterior segment has been described. The same manner applies for the case where the observation site is the fundus. In this case, an abnormal state can be detected by the detection method corresponding to the fundus image, as described above.

Further, the abnormality occurrence information stored in the storage unit 212 in step S20 of FIG. 6 may be used for rescanning in step S16 of FIG. 6 or for remeasuring the subject, for example.

For example, when it is determined that a deviation of the visual line (the movement of the subject's eye E) is likely to occur based on the abnormality occurrence information, the controller 210 may control LCD 39 to move the fixation position at the rescanning in step S16 or at the remeasuring the subject. Thereby the occurrence of the deviation of the visual line can be suppressed.

For example, when it is determined that blinking is likely to occur based on the abnormality occurrence information, the controller 210 may specify the occurrence cycle of blinking at the rescanning in step S16 or at the remeasuring the subject and controls the optical scanner 42 to scan in synchronization with the specified occurrence cycle.

For example, when it is determined that the eyelash is likely to be represented in the image based on the abnormality occurrence information, the controller 210 may control the UI unit 240 to output information for prompting the eyelid opening operation to the examiner before rescanning or remeasuring the subject.

For example, when it is determined that flare is likely to occur based on the abnormality occurrence information, the controller 210 may control the optical system driver 1A to adjust the working distance.

Effects

The ophthalmologic apparatus according to the embodiments is explained.

An ophthalmologic apparatus (1) according to the embodiments comprises an optical system (optical system shown in FIG. 1, interference optical system included in the OCT unit 100), a movement mechanism (optical system driver 1A), an image acquisition unit (imaging optical system 30), an abnormality detector (analyzer 231), a scan controller (211C), and a tracking controller (211B). The optical system includes an optical scanner (42), deflects light (L0) from a light source (light source unit 101) using the optical scanner, projects the light onto a subject's eye (E), and receives light (interference light LC, light of a part of the returning light) based on returning light from the subject's eye. The movement mechanism moves the subject's eye and the optical system relative to each other. The image acquisition unit acquires an image of the subject's eye. The abnormality detector detects abnormality (abnormal state) based on a reference image (base image) and the image (target image) of the subject's eye acquired by the image acquisition unit. The scan controller controls the optical scanner to re-perform a first scan or a second scan so as to project light from the light source onto a start position of the first scan, which is being performed for the subject's eye at an acquisition timing of the image of the subject's eye, or a start position of the second scan, which is performed before the first scan, when the abnormality is detected by the abnormality detector. The tracking controller controls the movement mechanism so that the optical system follows a movement of the subject's eye based on the reference image and the image of the subject's eye, when the abnormality is not detected by the abnormality detector.

According to such a configuration, the abnormality is detected during the control of tracking based on the reference image and the image of the subject's eye acquired by the image acquisition unit, and the first scan, which is being performed for the subject's eye at the acquisition timing of the image of the subject's eye, or the second scan is re-performed. Thereby, even when the cause which inhibits the control of tracking occurs during the control of tracking, the influence on the accurate acquisition of the image and the measurement can be reduced with a simple control.

Further, the ophthalmologic apparatus according to the embodiments comprises an alignment controller (211A) that controls the movement mechanism to perform position matching of the optical system with respect to the subject's eye, when the abnormality is detected, wherein the scan controller re-performs the first scan or the second scan, after the position matching by the alignment controller is completed.

According to such a configuration, the first scan or the second scan is re-performed after alignment is completed. Thereby, the consistency between data acquired before rescan and data acquired by re-performed scan is taken and contributing to accurate acquisition of the image and the measurement can be achieved.

Further, in the ophthalmologic apparatus according to the embodiments, the image acquisition unit may acquire an anterior segment image of the subject's eye, and the tracking controller may control the movement mechanism based on an amount of displacement of characteristic positions in the reference image and the anterior segment image.

According to such a configuration, even when the movement of the subject's eye occurs during the control of tracking based on the anterior segment image, the influence on the accurate acquisition of the image and the measurement can be reduced with a simple control.

Further, in the ophthalmologic apparatus according to the embodiments, the abnormality detector may detect the abnormality when the amount of displacement of the characteristic positions is equal to or larger than a first threshold value.

According to such a configuration, even when the movement of the subject's eye with large displacement of the characteristic position occurs during the control of tracking based on the anterior segment image, the influence on the accurate acquisition of the image and the measurement can be reduced with a simple control.

Further, in the ophthalmologic apparatus according to the embodiments, the abnormality detector may detect the abnormality when a characteristic point is not detected in the reference image or the anterior segment image.

According to such a configuration, even when blinking occurs during the control of tracking based on the anterior segment image, the influence on the accurate acquisition of the image and the measurement can be reduced with a simple control.

Further, in the ophthalmologic apparatus according to the embodiments, the abnormality detector may detect the abnormality when at least part of a boundary of a characteristic region is not detected in the reference image or the anterior segment image.

According to such a configuration, even when an eyelash is represented in the image during the control of tracking based on the anterior segment image, the influence on the accurate acquisition of the image and the measurement can be reduced with a simple control.

Further, in the ophthalmologic apparatus according to the embodiments, the image acquisition unit may acquire a fundus image of the subject's eye, and the tracking controller may control the movement mechanism so as to cancel an amount of displacement of positions obtained by performing a phase only correlation processing on the reference image and the fundus image.

According to such a configuration, even when the movement of the subject's eye occurs during the control of tracking based on the fundus image, the influence on the accurate acquisition of the image and the measurement can be reduced with a simple control.

Further, in the ophthalmologic apparatus according to the embodiments, the abnormality detector may detect the abnormality when a characteristic point is not detected based on luminance information of the reference image or the fundus image.

According to such a configuration, even when occurrence of blinking or representation of an eyelash in the image is detected during the control of tracking based on the fundus image, the influence on the accurate acquisition of the image and the measurement can be reduced with a simple control.

Further, in the ophthalmologic apparatus according to the embodiments, the abnormality detector may detect the abnormality when flare is detected in the reference image or the fundus image.

According to such a configuration, even when occurrence of flare is detected during the control of tracking based on the fundus image, the influence on the accurate acquisition of the image and the measurement can be reduced with a simple control.

Further, the ophthalmologic apparatus according to the embodiments may comprise a controller (210, main controller 211) that stores abnormality occurrence information including a cause of the abnormality in a storage unit (212) in association with subject information, when the abnormality is detected by the abnormality detector.

According to such a configuration, abnormality occurrence cause during the control of tracking can be specified.

Thereby, measures to prevent the occurrence of the same abnormality can be taken at remeasuring the subject, or the like.

Further, a method of controlling an ophthalmologic apparatus (1) according to the embodiments is the method of controlling the ophthalmologic apparatus comprising an optical system (optical system shown in FIG. 1, interference optical system included in the OCT unit 100) that includes an optical scanner (42), deflects light (measurement light LS) from a light source (light source unit 101) using the optical scanner, projects the light onto a subject's eye (E), and receives light based on returning light from the subject's eye, and a movement mechanism (optical system driver 1A) that moves the subject's eye and the optical system relative to each other. The method of controlling the ophthalmologic apparatus comprises an image acquisition step, an abnormality detection step, a scan control step, and a tracking control step. The image acquisition step acquires an image (target image) of the subject's eye. The abnormality detection step detects abnormality based on a reference image (base image) and the image of the subject's eye. The scan control step controls the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected. The tracking control step controls the movement mechanism so that the optical system follows a movement of the subject's eye based on the reference image and the image of the subject's eye, when the abnormality is not detected.

According to such a configuration, the abnormality is detected during the control of tracking based on the reference image and the image of the subject's eye acquired in the image acquisition step, and the first scan, which is being performed for the subject's eye at the acquisition timing of the image of the subject's eye, or the second scan is re-performed. Thereby, even when the movement of the subject's eye or blinking occurs during the control of tracking, the influence on the accurate acquisition of the image and the measurement can be reduced with a simple control.

Further, the method of controlling the ophthalmologic apparatus further may comprise an alignment control step of controlling the movement mechanism to perform position matching of the optical system with respect to the subject's eye, when the abnormality is detected, wherein in the scan control step, the first scan or the second scan may be re-performed, after the position matching in the alignment control step is completed.

According to such a configuration, the first scan or the second scan is re-performed after alignment is completed. Thereby, the consistency between data acquired before rescan and data acquired by re-performed scan is taken and contributing to accurate acquisition of the image and the measurement can be achieved.

Examples of Modifications

The above-described embodiments are merely examples for carrying out the present invention. Those who intend to implement the present invention can apply any modification, omission, addition, or the like within the scope of the gist of the present invention.

In the above embodiments, examples are described in which the configuration of the optical system has the configuration shown in FIG. 1 or FIG. 2; however, they are not so limited. The optical system according to the embodiments may include an optical system to project a laser light beam on a treatment site in the fundus, an optical system to move a visual target in a state where the subject's eye is being fixated.

In the embodiments described above, the case where the imaging site is the fundus or the anterior segment. However, the imaging site is not limited to the fundus or the anterior segment. Further, the imaging sites may be three or more sites.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
   an optical system that includes an optical scanner, deflects light from a light source using the optical scanner, projects the light onto a subject's eye, and receives light based on returning light from the subject's eye;
   a movement mechanism that moves the subject's eye and the optical system relative to each other;
   an image acquisition unit that acquires an image of the subject's eye;
   an abnormality detector that detects abnormality based on a reference image and the image of the subject's eye acquired by the image acquisition unit;
   a scan controller that controls the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected by the abnormality detector; and
   a tracking controller that controls the movement mechanism so that the optical system follows a movement of the subject's eye based on the reference image and the image of the subject's eye, when the abnormality is not detected by the abnormality detector,
   wherein the image acquisition unit acquires a fundus image of the subject's eye, and
   the tracking controller controls the movement mechanism so as to cancel an amount of displacement of positions obtained by performing a phase only correlation processing on the reference image and the fundus image.

2. The ophthalmologic apparatus of claim 1, further comprising:
   an alignment controller that controls the movement mechanism to perform position matching of the optical system with respect to the subject's eye, when the abnormality is detected, wherein
   the scan controller re-performs the first scan or the second scan, after the position matching by the alignment controller is completed.

3. The ophthalmologic apparatus of claim 1, wherein
   the image acquisition unit acquires an anterior segment image of the subject's eye, and
   the tracking controller controls the movement mechanism based on an amount of displacement of characteristic positions in the reference image and the anterior segment image.

4. The ophthalmologic apparatus of claim 3, wherein
   the abnormality detector detects the abnormality when the amount of displacement of the characteristic positions is equal to or larger than a first threshold value.

5. The ophthalmologic apparatus of claim 3, wherein
   the abnormality detector detects the abnormality when a characteristic point is not detected in the reference image or the anterior segment image.

6. The ophthalmologic apparatus of claim 3, wherein
   the abnormality detector detects the abnormality when at least part of a boundary of a characteristic region is not detected in the reference image or the anterior segment image.

7. The ophthalmologic apparatus of claim 1, wherein
   the abnormality detector detects the abnormality when a characteristic point is not detected based on luminance information of the reference image or the fundus image.

8. The ophthalmologic apparatus of claim 1, wherein
   the abnormality detector detects the abnormality when flare is detected in the reference image or the fundus image.

9. The ophthalmologic apparatus of claim 1, further comprising:
   a controller that stores abnormality occurrence information including a cause of the abnormality in a storage unit in association with subject information, when the abnormality is detected by the abnormality detector.

10. A method of controlling an ophthalmologic apparatus comprising:
    an optical system that includes an optical scanner, deflects light from a light source using the optical scanner, projects the light onto a subject's eye, and receives light based on returning light from the subject's eye;
    a movement mechanism that moves the subject's eye and the optical system relative to each other, the method of controlling the ophthalmologic apparatus comprising:
    an image acquisition step of acquiring an image of the subject's eye;
    an abnormality detection step of detecting abnormality based on a reference image and the image of the subject's eye;
    a scan control step of controlling the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected;
    a tracking control step of controlling the movement mechanism so that the optical system follows a movement of the subject's eye based on the reference image and the image of the subject's eye, when the abnormality is not detected;
    acquiring a fundus image of the subject's eye; and
    the tracking control step further controls the movement mechanism so as to cancel an amount of displacement of positions obtained by performing a phase only correlation processing on the reference image and the fundus image.

11. The method of controlling the ophthalmologic apparatus of claim 10, further comprising:

an alignment control step of controlling the movement mechanism to perform position matching of the optical system with respect to the subject's eye, when the abnormality is detected, wherein in the scan control step, the first scan or the second scan is re-performed, after the position matching in the alignment control step is completed.

12. An ophthalmologic apparatus comprising:

an optical system that includes an optical scanner, deflects light from a light source using the optical scanner, projects the light onto a subject's eye, and receives light based on returning light from the subject's eye;

a movement mechanism that moves the subject's eye and the optical system relative to each other;

an image acquisition unit that acquires an image of the subject's eye;

an abnormality detector that detects abnormality based on a reference image and the image of the subject's eye acquired by the image acquisition unit;

a scan controller that controls the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected by the abnormality detector;

a tracking controller that controls the movement mechanism so that the optical system follows a movement of the subject's eye based on the reference image and the image of the subject's eye, when the abnormality is not detected by the abnormality detector; and a controller that stores abnormality occurrence information including a cause of the abnormality in a storage unit in association with subject information, when the abnormality is detected by the abnormality detector.

13. A method of controlling an ophthalmologic apparatus comprising:

an optical system that includes an optical scanner, deflects light from a light source using the optical scanner, projects the light onto a subject's eye, and receives light based on returning light from the subject's eye;

a movement mechanism that moves the subject's eye and the optical system relative to each other, the method of controlling the ophthalmologic apparatus comprising:

an image acquisition step of acquiring an image of the subject's eye;

an abnormality detection step of detecting abnormality based on a reference image and the image of the subject's eye;

a scan control step of controlling the optical scanner to re-perform a first scan or a second scan so as to project light from the light source onto a start position of the first scan, which is being performed for the subject's eye at an acquisition timing of the image of the subject's eye, or a start position of the second scan performed before the first scan, when the abnormality is detected;

a tracking control step of controlling the movement mechanism so that the optical system follows a movement of the subject's eye based on the reference image and the image of the subject's eye, when the abnormality is not detected; and storing abnormality occurrence information including a cause of the abnormality in a storage unit in association with subject information, when the abnormality is detected.

* * * * *